United States Patent [19]

Linman et al.

[11] Patent Number: 4,738,249

[45] Date of Patent: Apr. 19, 1988

[54] METHOD AND APPARATUS FOR AUGMENTING BLOOD CIRCULATION

[75] Inventors: E. Kelly Linman; Eugene Weinshenker, both of Cincinnati, Ohio

[73] Assignee: The Procter & Gamble Company, Cincinnati, Ohio

[21] Appl. No.: 707,261

[22] Filed: Mar. 1, 1985

[51] Int. Cl.[4] .............. A61B 17/12

[52] U.S. Cl. .............. 128/24 R; 128/327; 128/64

[58] Field of Search .............. 128/24 R, 327, 64, 44; 604/315, 314

[56] References Cited

U.S. PATENT DOCUMENTS

| | | | |
|---|---|---|---|
| 2,082,190 | 6/1937 | Vogt et al. | 128/24 R |
| 2,140,898 | 12/1938 | Collens et al. | 128/44 X |
| 2,168,611 | 8/1939 | Thompson | 128/24 R |
| 2,832,336 | 4/1958 | Davis et al. | 128/24 R |
| 3,083,708 | 4/1963 | Gottfried | 128/64 |
| 3,101,085 | 8/1963 | Murphy, Jr. | 128/325 |
| 3,167,067 | 1/1965 | Rand | 128/327 X |
| 3,190,444 | 6/1965 | Kelson | 128/327 |
| 3,403,673 | 10/1968 | MacLeod | 128/64 X |
| 3,450,450 | 6/1969 | Hopkins et al. | 312/1 |
| 3,465,748 | 9/1969 | Kravchenko | 128/24 R |
| 3,465,749 | 9/1969 | Moreland et al. | 128/327 X |
| 3,654,919 | 4/1972 | Birtwell | 128/64 |
| 3,783,859 | 1/1974 | Sauer et al. | 128/64 X |

(List continued on next page.)

OTHER PUBLICATIONS

An article from the *Journal of American Medical Asso.*, 10/10/35, entitled "Nonoperative Treatment of Inadequate Peripheral Distribution of Blood" by Louis G. Herrmann, M.D.

An article from the *Annals of Surgery*, vol. 100, Oct. 1934, entitled "The Conservative Treatment of Arteriosclerotic Peripheral Vascular Diseases" by Louis G. Herrmann, M.D., and Mont R. Reid, M.D.

An article from the *Archives of Surgery*, vol. 29, No. 5, Nov. 1934, entitled "Passive Vascular Exercises" by Louis G. Herrmann, M.D. and Mont R. Reid, M.D.

Chapter 31 "The Arterial System: Arteries and Arterioles", *Physiology and Biophysics*, Edited by Theodore C. Ruch, Ph. D. and Harry D. Patton, Ph. D., M.D., W. B. Saunders Company, 1965.

*Primary Examiner*—Ira S. Lazarus
*Assistant Examiner*—Richard R. Cole
*Attorney, Agent, or Firm*—E. Kelly Linman; John V. Gorman; Richard C. Witte

[57] ABSTRACT

Method for enhancing blood circulation in a predetermined portion of a patient's body remote from the patient's heart. In a preferred embodiment the method comprises: placing an isolated portion of the patient's body within a chamber comprised of substantially gas impervious material; forming a substantially airtight seal between the chamber and the isolated portion of the patient's body; constricting venous blood flow from the isolated portion of the patient's body; evacuating sufficient air from within the chamber to create a partial vacuum within the chamber; maintaining the partial vacuum within the chamber for a period of time sufficient for the patient's arterial pressure to engorge the blood vessels contained within the isolated portion of the patient's body with blood and to distend the blood vessels; releasing the constriction on venous blood flow; and allowing sufficient air to enter the chamber to at least partially dissipate the vacuum existing within said chamber, thereby allowing the engorged, distended blood vessels within the isolated portion of the patient's body to return from their distended condition to a non-distended condition and forcing blood contained within the blood vessels from the isolated portion of the patient's body. Upon completion of the engorgement cycle, restoration of unrestricted venous blood flow is preferably followed by the application of pressure to the limb to avoid stagnation of blood in the limb being treated, after which the engorgement cycle is automatically repeated.

29 Claims, 3 Drawing Sheets

U.S. PATENT DOCUMENTS

| | | | |
|---|---|---|---|
| 3,811,431 | 5/1974 | Apstein | 128/64 |
| 3,859,989 | 1/1975 | Spielberg | 128/24 R |
| 3,880,149 | 4/1975 | Kawaguchi | 128/24 |
| 3,885,554 | 5/1975 | Rockwell, Jr. | 128/24 |
| 3,892,229 | 7/1975 | Taylor et al. | 128/24 |
| 3,942,518 | 3/1976 | Tenteris et al. | 128/24 |
| 3,971,398 | 7/1976 | Taylor et al. | 137/119 |
| 3,976,056 | 8/1976 | Brawn | 128/24 |
| 4,030,488 | 6/1977 | Hasty | 128/24 |
| 4,044,759 | 8/1977 | Ghayouran | 128/24 R |
| 4,054,129 | 10/1977 | Byars et al. | 128/24 |
| 4,057,046 | 11/1977 | Kawaguchi | 128/24 |
| 4,086,920 | 5/1978 | Miniere | 128/24 R |
| 4,153,050 | 5/1979 | Bishop et al. | 128/64 |
| 4,206,751 | 6/1980 | Schneider | 128/24 |
| 4,269,175 | 5/1981 | Dillon | 128/24 |
| 4,299,219 | 11/1981 | Norris, Jr. | 128/215 |
| 4,311,135 | 1/1982 | Brueckner et al. | 128/24 |
| 4,329,985 | 5/1982 | Bonchek | 128/214 |
| 4,353,359 | 10/1982 | Milbauer | 128/66 |
| 4,374,518 | 2/1983 | Villanueva | 128/64 |
| 4,378,008 | 3/1983 | Osbon, Sr. | 128/79 |
| 4,481,937 | 11/1984 | Arkans | 128/24 |
| 4,664,651 | 5/1987 | Weinshenker et al. | 604/115 |

METHOD AND APPARATUS FOR AUGMENTING BLOOD CIRCULATION

TECHNICAL FIELD

The present invention has relation to method and apparatus for augmenting blood circulation in one or more of a patient's limbs.

The present invention also has relation to method and apparatus for cyclically increasing both venous distention and transmural pressure in the capillaries in one or more of the patient's limbs.

In a particularly preferred embodiment, the present invention has relation to method and apparatus for improving blood circulation by cyclically subjecting the limb or limbs in question to subatmospheric pressure and thereafter exposing the limb or limbs to atmospheric pressure. This causes the blood vessels in the limb being treated to expand and contract in direct response to the cyclical subatmospheric pressure cycles. If desired, mechanical pressure or a superatmospheric pneumatic pressure pulse may be applied to the limb following each subatmospheric treatment to cyclically pump the blood from the engorged vessels in limb being treated back into the patient's body. The pumping action thus imparted to the blood vessels not only increases the total amount of blood flow through the limb, but also minimizes the chance of blood clotting due to stagnation, particularly in inactive patients.

The present invention has further relation to a method of using such cyclical negative and positive pressure pulses in conjunction with a system for constricting venous flow from the limb being treated in a manner which permits elevation of the pressure in the veins to a level approximating that in the arteries. As a result, the veins become cyclically engorged with blood and greatly distended. Controlling venous pressure and distention in this manner controls the transmural pressure in the capillaries, which in turn influences the rate of exchange of fluids and nutrients between the blood stream in the capillaries and the interstitial fluids surrounding the capillaries.

The present invention has still further relation, in a particularly preferred embodiment, to method and apparatus for augmenting blood flow and blood vessel distention without physically contacting the patient's limbs with structural elements. Such method and apparatus may be used not only during surgical procedures, such as balloon angioplasty, but also as a routine method of treatment in patients suffering from disorders which often inhibit blood circulation in the patient's limbs and which, if left untreated, can ultimately lead to infection, amputation and even death.

BACKGROUND ART

The present invention is designed to deal with two broad but distinct classes of vascular problems: (1) the maintenance of suffcient arterial flow to perfuse the tissues in the extremities; and (2) the maintenance of adequate venous flow and the prevention of stagnation and clot formation in the veins.

There are two sources of these two classes of problems and either can exist without the other or they can coexist.

The first class of problems, interference with arterial blood flow, is typically caused by atherosclerosis, either localized or diffuse.

Inadequate arterial flow can lead to such problems as pain upon exertion, slow healing of injuries, easy infection of minor injuries, breakdown of soft tissues leading to slow healing ulcers and in the extreme, gangrene, with resultant need to amputate the limb.

Currently available medical drug therapies for this condition are of limited value. Surgical procedures, including for example balloon angioplasty, are more frequently used to correct these problems.

The second class of problems, stagnation of blood flow in the veins may be caused by structural changes in the veins, by partial or complete failure of one or more of the patient's valves and or by inadequate muscular activity in the patient, since venous flow in the patient's limbs is to a large part due to the alternate compression and release of the veins caused by pressure exerted upon them by the muscles in the limbs.

Currently available device based therapies are limited to the second class of problems involving venous flow and consist of means to limit the cross-sectional area of the veins through the use of support garments, such as elastic surgical support stockings, or they seek to periodically compress the veins more completely through the application of intermittent pressure about the limb to collapse the veins and expel the blood from them. In some cases the pressure is applied as a pulsating wave through a series of pneumatically actuated cuffs, starting distally and moving proximally toward the patient's heart in an attempt to "milk" or expel the venous volume still more completely.

Prior art devices intended to alter the normal flow of blood in a patient's circulatory system are descibed in a plethora of previously issued patents, the following being exemplary: U.S. Pat. No. 3,101,085 issued to Murphy, Jr. on Aug. 20, 1963 which discloses an alternating tourniquet system to prevent excess blood from backing up into the patient's lungs when the left side of the heart is unable to pump the entire volume of blood getting to it; U.S. Pat. No. 3,811,431 issued to Apstein on May 21, 1974 which discloses a programmed venous assist pump; U.S. Pat. No. 3,892,229 issued to Taylor et al. on July 1, 1975 which discloses apparatus for augmenting venous blood flow; U.S. Pat. No. 3,942,518 issued to Tenteris et al. on Mar. 9, 1976 which discloses a therapeutic intermittent compression apparatus; U.S. Pat. No. 3,976,056 issued to Brawn on Aug. 24, 1976 which discloses an intermittent pressure pneumatic stocking; U.S. Pat. No. 4,030,488 issued to Hasty on June 21, 1977 which discloses an intermittent compression device; U.S. Pat. No. 4,054,129 issued to Byars et al. on Oct. 18, 1977 which discloses a system for applying pulsating pressure to the body; U.S. Pat. No 4,057,046 issued to Kawaguchi on Nov. 8, 1977 which discloses a blood circulation stimulator; U.S. Pat. No. 4,153,050 issued to Bishop et al. on May 8, 1979 which discloses a pulsatile stocking and bladder therefor; U.S. Pat. No. 4,206,751 issued to Schneider on June 10, 1980 which discloses an intermittent compression device; U.S. Pat. No. 4,269,175 issued to Dillon on May 26, 1981 which discloses method and apparatus for promoting circulation of blood; U.S. Pat. No. 4,311,135 issued to Brueckner et al. on Jan. 19, 1982 which discloses apparatus to assist leg venous and skin circulation; and U.S. Pat. No. 4,374,518 issued to Villaneuva on Feb. 22, 1983 which discloses an electronic device for pneumomassage to reduce lymphedema.

Many of the pneumatic leggings or boots disclosed in the aforementioned references are adapted to fit around the calf and foot of a patient's legs, such leggings being connected to pump apparatus which sends alternate intermittent pulses to each of the leggings to periodically compress and release the legs and thereby accelerate blood flow. Typically, a series of one-way valves is used in the leggings so that blood is permitted to move only in an upward direction toward the patient's heart and backflow is minimized or prevented.

Unfortunately, none of these prior devices are designed to provide significant benefit in cases of deficient flow due to arterial problems.

Accordingly, it is an object of the present invention to augment blood flow in spite of reduced arterial lumen size and to increase the total venous blood exchange such that the veins are substantially distended and collapsed with each pressure cycle rather than merely compressed from their normal condition to a minimally distended condition with each pressure cycle.

It is another object of the present invention to provide method and apparatus capable of boosting blood circulation in a patient's limb while waiting for collateral flow to develop.

It is still another object of the present invention to provide method and apparatus for accomplishing the foregoing treatment which are not painful to the patient, which are safe and simple to use, which are highly reliable, yet which are relatively inexpensive to manufacture.

DISCLOSURE OF THE PRESENT INVENTION

The present invention pertains in a particularly preferred embodiment to method and apparatus for providing cyclical blood vessel distention to provide improved blood circulation to and from the limb being subjected to treatment as well as improved transfer of fluids and nutrients in the blood stream in the capillaries contained within the limb being treated and the interstitial fluids surrounding the capillaries. As with any medical therapy, any practice of the present invention should be under the guidance of a competent medical practitioner thoroughly familiar with the medical history of the patient to be treated.

The method and apparatus of the present invention utilize the patient's arterial pressure to cyclically engorge the blood vessels in the limb being treated, preferably while subjecting the limb in question to subatmospheric pressure.

This is preferably accomplished by periodically exposing the patient's limb to a repeating cycle of pneumatic pressure going from negative to atmospheric to positive. The ability to control the timing and the magnitude of the pneumatic pressure (subatmospheric to atmospheric to above atmospheric) in an airtight chamber surrounding the limb and the timing and the pressure level of a constricting band, such as a pneumatically actuated blood pressure cuff, also surrounding the limb and located at the entrance to the airtight chamber, make is possible to control and vary the following parameters: the flow of blood and the pressure of the blood in the arteries, veins and capillaries; the distention and compression of the veins; and the transmural pressure in the capillaries. By controlling the transmural pressure in the capillaries in accordance with the present invention it is believed possible, for the first time, to influence the rate of exchange of fluids and nutrients between the blood stream in the capillaries and the interstitial fluids surrounding the capillaries.

In a particularly preferred embodiment, a substantially gas-impervious chamber is placed over the patient's limb to be treated. A substantially airtight seal is achieved with the patient's body at the proximal end of the chamber, and the pressure in the chamber is reduced to a level below atmospheric. The subatmospheric pressure to which the limb is thereafter subject allows the blood vessels in the limb to expand relative to the blood vessels in the remainder of the patient's body which remain subject to atmospheric pressure. As a result, the blood vessels in the isolated limb become distended and engorged with blood. In addition to augmenting blood circulation in patients having circulatory disorders, use of such a substmospheric pressure treatment may be a significant aid in conducting surgical type procedures where a key objective is to more fully distend the blood vessel being treated, e.g., balloon angioplasty.

A pneumatic blood pressure cuff or other constricting device may, if desired, be located at the proximal end of the chamber and can be used to aid in forming a substantially airtight seal between the patient's limb and the vacuum chamber. In addition, it may, if desired, be utilized to increase the degree of venous distention produced by each substmospheric pressure cycle. When the pneumatic pressure of the blood pressure cuff is raised to a level sufficient to reduce or, if desired, substantially block venous blood flow from the patient's limb, the blood vessels in the limb being treated become further engorged by arterial blood flow. When venous blood flow is substantially blocked, the driving force exerted upon the limb being treated is equal to the sum of the patient's arterial blood pressure and the absolute value of the vacuum pressure existing within the chamber. If it is desired to maximize blood vessel distention, the constriction on venous flow may be gradually increased and the vacuum level may be maintained for a period of time sufficient for the pressure in the veins to approximate that existing within the arteries of the limb being treated. This requires that venous blood flow be substantially blocked by a cuff constriction pressure which is less than the patient's systolic arterial pressure. If the cuff pressure is immediately elevated above the patient's systolic arterial blood pressure, blood flow to and from the limb being treated will be completely stopped and any pressure equalization which may take place between the veins and the arteries will occur at a much lower value than if the cuff pressure is either initially raised to a value just below systolic or slowly elevated during the engorgement cycle as the blood pressure in the veins approaches that in the arteries. Equalizing the blood pressure in the veins and the arteries at the maximum possible value will result in maximum distention of the blood vessels.

Once the desired level of venous distention and/or pressure eqalization has occurred, the vacuum in the chamber is vented to atmosphere and the constricting blood pressure cuff is deflated to again permit unrestricted venous blood flow, thereby allowing the detended, blood engorged veins to collapse from a substantially round to a more normal flattened condition. This collapsing action, which is promoted by the flaccid nature of veins and the lack of pressure within the veins when the cuff pressure is released, helps to pump the blood from the treated limb back into the patient's body, thereby reducing the chance of clot formation in the limb being treated.

If desired, collapse of the veins following the engorgement cycle can be aided by the application of some form of pressure to the patient's limb to further reduce the size of the patient's veins and thereby "milk" the blood from the limb being treated back into the patient's body. In simplest form, constant mechanical pressure might be applied to the limb via an elastic garment such as a surgical support stocking applied to the limb prior to installing the pneumatically actuated constriction cuffs. More elaborate application systems can involve peristaltic type mechanical pressure applied via pneumatically actuated leggings of the type described earlier herein. In those situations wherein the limb is placed in an airtight chamber, a pulse of positive pneumatic pressure is most preferably applied to the chamber at the conclusion of each vacuum cycle. The latter approach is particularly desirable, since it permits uniform pressure application to the entire limb without causing any localized discomfort or irritation to the patient. In addition it permits freedom of movement of the patient's limb, albeit within the confines of the chamber.

BRIEF DESCRIPTION OF THE DRAWINGS

While the specification concludes with claims particularly pointing out and distinctly claiming the present invention, it is believed the present invention will be better understood from the folllowing description in conjunction with the accompanying drawing Figures in which:

DETAILED DESCRIPTION OF THE INVENTION

Figure 1:
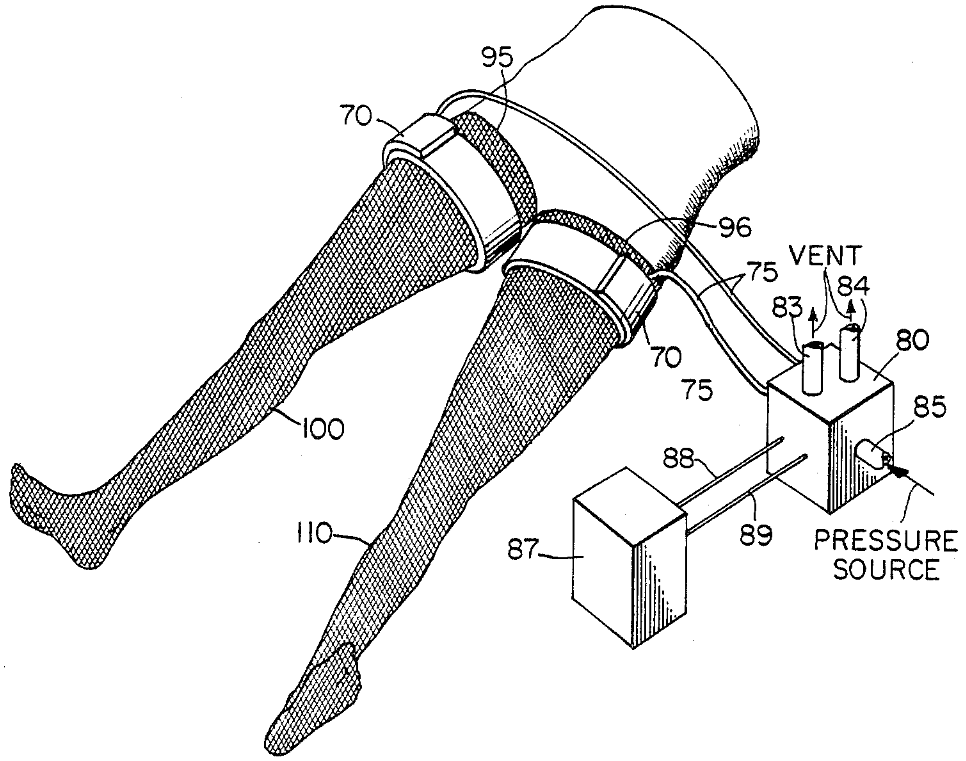
FIG. 1 is a simplified perspective illustration of an embodiment of the present invention using an alternating tourniquet system in combination with a pair of elastic surgical support stockings which are applied to the patient's legs prior to installation of the pneumatically actuated pressure cuffs.

In FIG. 1 there is shown a very simple embodiment of a cyclic blood vessel distention and compression device of the present invention. While a cyclical constriction device 70 is shown on each of the patient's legs, it will be readily appreciated that the apparatus may, if desired, be employed on only one of the patient's limbs or that multiple apparatus may be simultaneously employed on as many of the patient's limbs as is desired. The limb constriction apparatus 70 shown installed on each of the patient's legs can comprise a simple pneumatically actuated blood pressure cuff 70. Each blood pressure cuff 70 is connected by means of a pneumatic tube 75 to a control valve 80, which in turn cyclically connects each limb constricting pressure cuff with a pressure source such as compressed air or compressed gas shown generally at 85. Pneumatic tubes 83 and 84 which are also associated with control valve 80 serve as vents to dissipate the pressure generated within each of the constriction cuffs 70 whenever the logic module 87 which is connected to control valve 80 by means of signal transmitting lines 88, 89 actuates control valve 80, thereby shifting either or both pneumatic tubes 75 from fluid communication with pressure source 85 into fluid communication with pneumatic vent tubes 83, 84. This results in a rapid release of pressure within the respective pneumatic cuffs 70, thereby removing the constriction from either or both of the patient's legs 100, 110.

The constriction cuff 70 on leg 100 and the constriction cuff 70 on leg 110 may be operated out of phase with one another so that the reease of pressure from both cuffs does not occur simultaneously. It is believed that operating the cuffs out of phase with one another will minimize any disturbance to the balance of the patient's circulatory system.

The pneumatically actuated constriction cuffs 70 utilized on each of the patient's legs are preferably actuated so that the pressure in each cuff is initially elevated to a level sufficient to reduce or, if it is desired to maximize venous distention, to substantially block venous flow. Depending upon the patient and the desired treatment objective, the cuff pressure can range from as little as 5 millimeters of mercury to a level just short of the particular patient's systolic arterial blood pressure. Exceeding the patient's systolic arterial blood pressure is believed inappropriate since it will also stop blood flow to the patient's limb and may cause injury to the patient if maintained for too long a period.

If the cuff pressure is raised to a level sufficient to block venous flow in the patient's limb, e.g., leg 100 or leg 110, the patient's systolic arterial pressure acts as a driving force in filling the limb with blood. Blockage of venous flow in this manner will permit elevating the blood pressure within the capillaries and the veins of the limb being treated to a level approaching that within the arteries. This results in maximum distention of the veins from their normal relatively flat condition toward a more round cross-sectional configuration. If venous blood flow is merely reduced but not blocked by the constricting cuff, the level of venous distention will be somewhat less, and any pressure equalization which may occur between the veins and the arteries will be at a reduced value. To be certain that venous blood flow remains blocked as the pressure in the veins approaches that in the arteries, it may in some instances be desirable to gradually increase the pressure of the constriction cuff all the way up to systolic to ensure maximum blood vessel distention with each cycle. If desired, this gradual pressure build-up feature can be programmed into logic module 87.

When sufficient time has elapsed to permit engorgement of the patient's veins to whatever level is desired by the medical practitioner, the constriction cuff 70 in the limb being treated is either vented to atmosphere or its inflation pressure is sufficiently reduced that the constriction on the limb is effectively removed. This permits the blood trapped within the engorged veins to return to the patient's body and travel toward the patient's heart in a substantially unrestricted manner.

By cyclically repeating the foregoing process in each of the patient's legs 100, 110, preferably in alternating sequence, the total blood circulation within the limb is significantly augmented. In addition, controlling the venous distention in the foregoing manner permits control of the transmural pressure in the capillaries, which in turn accelerates the rate of exchange between fluids and nutrients in the blood stream in the capillaries and the interstitial fluids surrounding the capillaries. Accordingly, it is believed that practice of the present invention, particularly in a patient having circulatory disorders in the limbs, can provide considerable improvement in the patient's ability to heal wounds on the limb and to minimize the chances that infections, or conditions such as gangrene, may develop due to the impaired circulation.

As will be appreciated by those skilled in the art, expulsion of blood from the veins depends to a large extent upon muscular activity in the patient's limbs. Accordingly, in patients who are non-ambulatory or who may not experience sufficient muscular activity to expel the blood from the veins, it is often desirable to apply some form of pressure to the patient's limb to avoid stagnation of blood in the limb after the engorgement cycle and thereby minimize the risk of clotting.

In the embodiment illustrated in FIG. 1 a pair of surgical support stockings 95, 96 has been applied to the patient's legs 100, 110, respectively, prior to installation of teh pneumatically actuated constriction cuffs 70. The elastic support stockings 95, 96 assist the veins in collapsing, thereby expelling the blood contained therein from each of the patient's limbs at the conclusion of each engorgement cycle, Elastomeric surgical support garments of this type are well known in the art and therefore not described in detail.

As will be appreciated by those skilled in the art, a pair of surgical stockings 95, 96 exerts a constant pressure upon the patient's limb not only at the conclusion of the blood engorgement cycle, but also during the engorgement cycle. In order to maximize blood vessel distention during the engorgement cycle it may, in some instances, be desirable to apply external pressure to the patient's limb only at the conclusion of the engorgement cycle.

Figure 2:
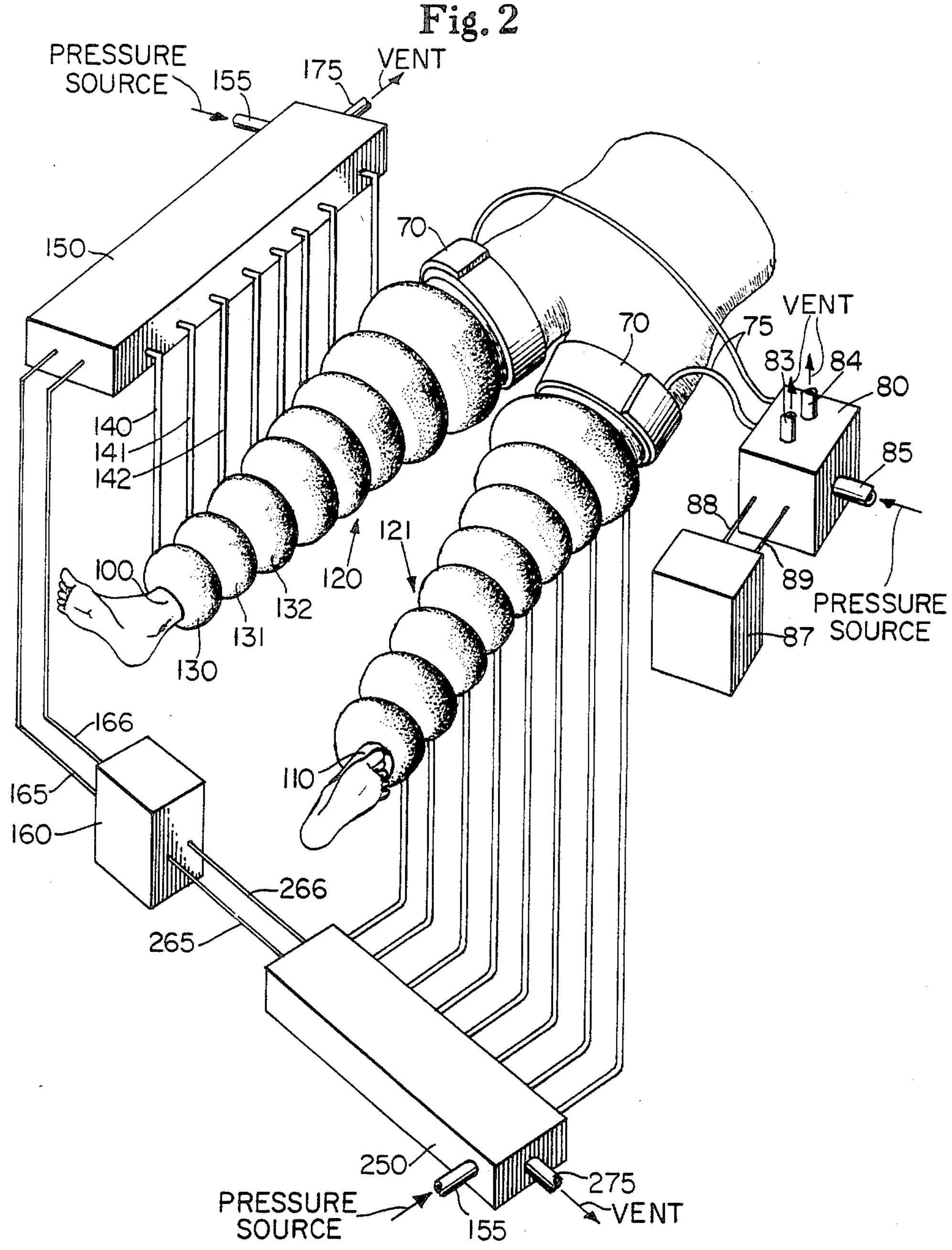
FIG. 2 is an illustration of another preferred embodiment of the present invention, wherein the pneumatically actuated pressure cuffs are employed in conjunction with a pair of pneumatically actuated leggings which can apply intermittent mechanical pressure to the patient's legs in a peristaltic fashion to compress the blood vessels and expel the blood contained therein toward the patient's heart.

FIG. 2 discloses an alternative embodiment of the present invention wherein pneumatically actuated constriction cuffs 70 identical to those shown in FIG. 1 are utilized in conjunction with a pair of pneumatically actuated peristaltic type leggings of the type generally described earlier herein. The pneumatically actuated leggings 120, 121 applied over the patient's legs 100, 110, respectively, preferably comprise a series of physically interconnected pneumatically actuated cuffs 130, 131, 132, etc., each of which comprises a discrete pneumatic chamber independently connected by means of a pnuematic tube, 140, 141, 142, respectively, to a control valve 150 which is in turn connected to a source of pneumatic pressure indicated generally at 155. Control valve 150 is actuated by logic module 160 interconnected by means of signal transmitting lines 165, 166 to valve 150 such that compressed air is fed first to lowermost pneumatic chamber 130, then to adjacent chamber 131, then to adjacent chamber 132, etc., to produce a peristaltic type compression of the patient's leg 100 in a generally proximal direction. By sequentially applying pneumatic pressure to each of the interconnected cuffs in the foregoing manner, the patient's limb can effectively be "milked" of blood such that the chance of stagnation and clotting in the limb being treated are substantially reduced. Pneumatically actuated legging 121 is substantially identical to legging 120 and is controlled via valve 250 which is substantially identical to valve 150. Valve 250 is also connected to logic module 160 via signal transmitting lines 265 and 266. As can be seen from FIG. 2, valves 150 and 250 are each in fluid communication with a source of pnuematic pressure indicated generally at 155.

Once all of the independent chambers 130, 131, 132, etc., in the legging 120 have been sequentially inflated, they are preferably simultaneously vented through control valve 150 via pneumatic vent line 175. At this point, the constriction cuff 70 on leg 100 is again inflated to a pressure sufficient to reduce or substantially block venous flow and the process is repeated. An identical operation is preferably performed on the patient's other leg 110, but opposite in phase from the operation being performed on leg 100.

Figure 3:
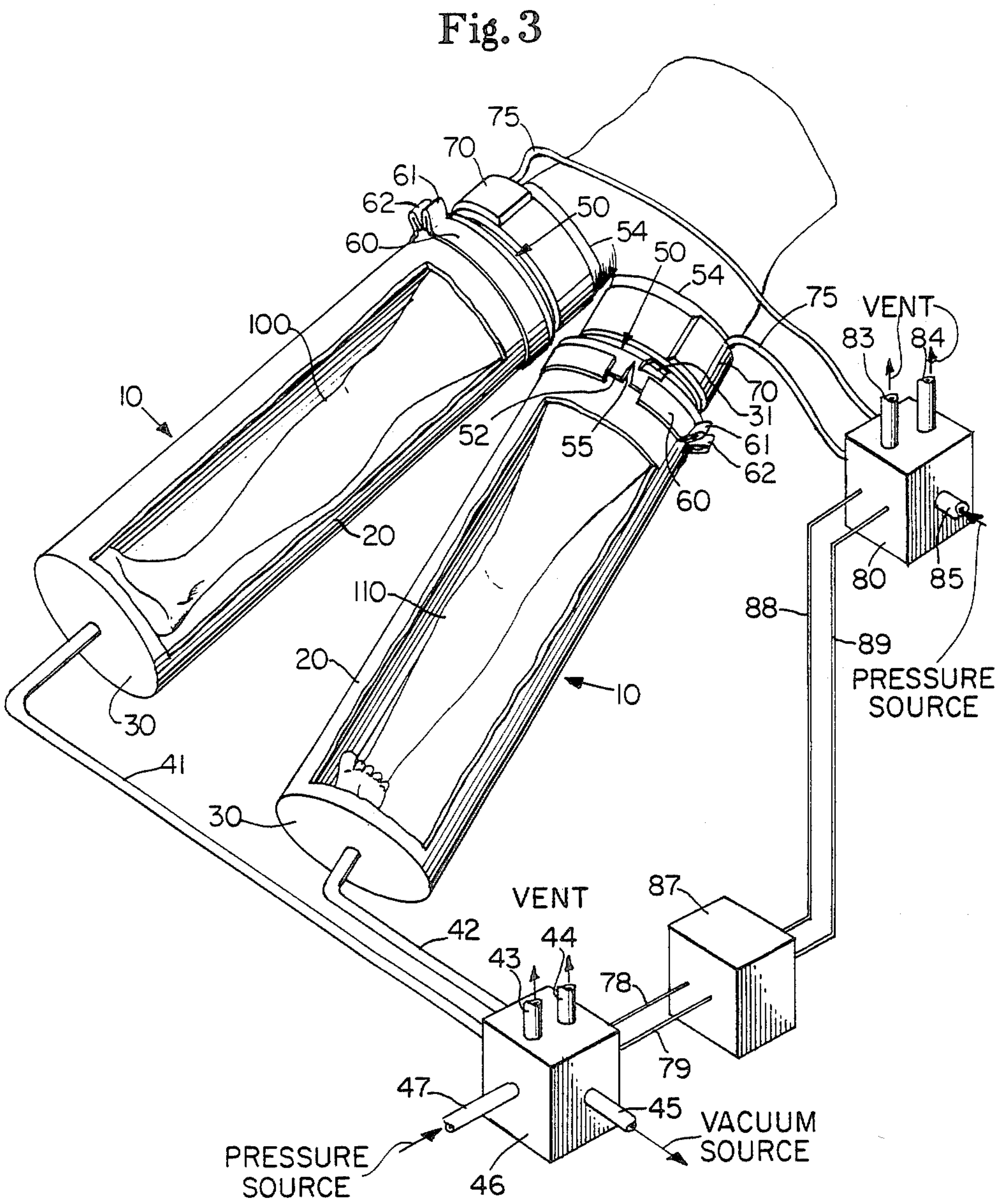
FIG. 3 is a simplified perspective illustration of a particularly preferred embodiment of the present invention employing a pair of pneumatically actuated pressure cuffs in conjunction with a pair of airtight pressure chambers installed on the legs of a patient, a portion of each chamber being broken away to illustrate the patient's legs.

FIG. 3 is an illustration of yet another preferred embodiment of the present invention. While a two-chambered apparatus is shown, one chamber for treating each of the patient's legs, it will be readily appreciated that a single-chambered apparatus may, if desired, be employed on only one of the patient's limbs or that multiple-chambered apparatus may be simultaneously employed on as many of the patient's limbs as is desired. It is also recognized that in certain variations of the present invention, a larger chamber could be employed to subject more than the patient's limbs to treatment.

Each unit shown in FIG. 3 preferably comprises a chamber 10 having a closed distal end 30 and an open proximal end 31 into which one of the patient's limbs is inserted. The chamber 10 can be comprised of substantially any material which is substantially gas impermeable and which has sufficient resistance to collapse that any subatmospheric pressures created within the chamber will not cause collapse of the chamber in use. In addition the chamber must be sufficiently strong to resist rupture in the event a positive pressure cycle is employed in practicing a particularly preferred embodiment of the present invention. One relatively simple and readily available material which is suitable for making chamber 10 comprises a simple cardboard mailing tube having a metal end wall 30, the cylindrical cardboard wall surfaces 20 of which have either been wrapped or coated to make them substantially impervious to the passage of gas through the walls of the tube. The length of the cylindrical wall portion 20 of the tube is typically about 2 to about 3 feet if the limb to be treated is an arm or about 3 to about 4 feet if the limb to be treated is a leg. The diameter of the tube is sufficiently large that it will permit insertion of the patient's limb without interference, i.e., on the order of about 5 to about 8 inches if the device is to be applied to the patient's arm, and perhaps about 10 to about 12 inches if the chamber is to be applied to the patient's leg. The precise dimensions and shape will, of course, vary depending upon the size of the patient.

It is recognized in practicing the present invention in any of the embodiments herein disclosed that the portion of the patient's body selected for treatment must be remote from the patient's heart, since the patient's arterial pressure acts as the primary driving force to engorge the blood vessels in the portion of the body being treated. When a subatmospheric pressure is created within an airtight chamber housing only a portion of the patient's body, such as a limb, it establishes an effective pressure differential between the treated and the untreated portions of the patient's body. This effective pressure differential is additive to the patient's arterial pressure. Thus, in a particularly preferred embodiment of the present invention, a subatmospheric pressure is created in an airtight chamber to enhance engorgement and distention of the blood vessels in the portion of the body being treated. In this regard, it should be noted that if the entire body of the patient, including the heart, were subjected to subatmospheric pressure, there would be no differential pressure to enhance blood vessel engorgement and distention in a particular portion of the patient's body.

In the case of the two-chambered unit illustrated in FIG. 3, an airtight seal is established between each of the patient's legs 100, 110 and its respective chamber 10 by means of an elastomeric sleeve which is stretched over the outermost portion of cylindrical wall 20 of each chamber 10. Each elastomeric sleeve 50 is preferably secured to its respective chamber 10 by means of a strip of tape 60 or similar material, the adhesive surface of which contacts both the exterior wall 20 of the chamber and the first end 52 of the elastomeric sleeve 50. As shown in FIG. 3, the band of tape 60 completely encircles the periphery of the chamber wall 20, and, upon making initial contact with one another adjacent chamber wall 20, each unadhered end is preferably turned upon itself so that the opposing adhesive faces of each end of the tape contact one another. This provides free ends 61, 62 without exposed adhesive. The resultant free ends 61, 62 provide quick and easy access when it is desired to remove the chamber 10 from the patient's limb.

From the broken out section shown in FIG. 3, it will be observed that a small stress concentrating notch 55 is preferably provided in the first edge 52 of the elastomeric sleeve 50. By utilizing an elastomeric sleeve 50 exhibiting a molecular orientation which permits rapid tear propagation in a direction generally parallel to the axis of the cylindrical wall 20 of the chamber 10, it is possible to readily remove the chamber simply by pulling on one of the free ends 61 or 62 of the encircling band of tape 60. As the tape 60 is peeled back from the surface of end 52 of the elastomeric sleeve and exterior wall 20 of the chamber, the peeling force exerted by the tape will cause the stress concentrating notch 55 to initiate a tear in the elastomeric sleeve 50 in a direction generally parallel to the axis of the cylindrical chamber 10. This permits quick and easy removal of the chamber from the patient's limb while the elastomeric sleeve is, at least for the moment, left in place.

The aforementioned quick-release feature is particularly beneficial in circumstances where it is desired to employ a constricting device, such as a pneumatically actuated constriction cuff 70, in conjunction with elastomeric sleeve 50, since it permits removal of the chamber 10 while the cuff is left in place in an inflated condition should this for any reason be desired.

In use, the chamber 10 is placed over the patient's limb and the elastomeric sleeve 50 is placed in contact with the patient's limb. A conventional pneumatic blood pressure cuff 70 or the like is preferably thereafter secured about end 54 of the elastomeric sleeve 50. To ensure that a substantially airtight seal is established between the sleeve 50 and the patient's body, the blood pressure cuff 70 is preferably inflated to a pressure of about 20 millimeters of mercury.

In the embodiment illustrated in FIG. 3 the inflatable cuffs 70 are connected to a control valve 80 by means of pneumatic tubes 75, as generally described in connection with the embodiment of FIG. 1. Logic module 87 is connected to control valve 80 via signal transmission lines 88, 89. The control valve 80, which, upon command from logic module 87, places one or both pneumatically actuated cuffs 70 in fluid communication with a source of pneumatic pressure shown generally at 85 also regulates the pressure supplied to each cuff in accordance with predetermined signals received from the logic module. The initial cuff pressure serves to not only help establish an airtight seal between the elastomeric sleeves 50 and the wearer's legs 100, 110, but also acts to prevent substantial axial movement of the chambers 10 in a proximal direction toward the patient's body as the pressure inside each chamber is reduced below atmospheric and in a distal direction away from the patient's body at the pressure inside the chamber is elevated above atmospheric. The tendency for the chambers 10 to move up or down the patient's limb in axial direction is caused by the force imbalance created on the ends of the chambers. In particular, atmospheric pressure is exerted on substantially all of distal end walls 30 while it can act only on that portion of elastomeric sleeves 50 intermediate cylindrical walls 20 and the patient's limbs 100, 110. Due to the aforementioned difference in cross-sectional areas, there is a net force tending to advance each chamber 10 in a proximal direction toward the patient's body when the pressure inside is below atmospheric and in a distal direction away from the patient's body when the pressure inside is above atmospheric.

The pneumatically actuated pressure cuff 70 and the elastomeric sleeve 50 one each chamber 10 help to prevent movement of the chamber in response to changes in internal pressure. Additionally or perhaps alternatively, the chambers 10 could be secured to the substrate on which the patient is resting to prevent axial movement of the chambers and/or a soft material such as resilient foam could be included inside the chamber end walls to prevent injury if contact should occur between the foam and the patient's foot or toes due to relative axial movement of the chamber with respect to the patient's limbs.

It is, of course, possible to establish a subatmospheric pressure within the vacuum chambers 10 by many different means well known in the art. In the embodiment illustrated in FIG. 3, pneumatic tubes 41, 42 connect each of the chambers 10 to a control valve indicated generally as 46. Control valve 46 is actuated by signals from logic module 87, which is connected thereto by means of signal transmission lines 78, 79. Control valve 46 is also connected to any suitable vacuum source shown generally at 45. The vacuum source may be as simple as an electrically operated vacuum pump (not shown). Pneumatic tubes 43 and 44 which are also associated with control valve 46 serve as vents to dissipate the vacuum generated within chambers 10 whenever logic module 87 actuates control valve 46, thereby shifting pneumatic tubes 41, 42 from fluid communication with vacuum source 45 into fluid communication with either or both pneumatic vent tubes 43, 44. This results in a rapid return of either or both chambers 10 to atmospheric pressure.

In a particularly preferred mode, the apparatus generally shown in FIG. 3 is operated in the sequence hereinafter described. First, the constriction cuffs 70 are inflated to a pressure of approximately 20 millimeters of mercury to establish an airtight seal between the chambers 10 and the patient's legs 100, 110. The logic module 87 thereafter connects one of the chambers with the vacuum source 45 while the other chamber remains vented to atmophere. Interconnection of the first chamber to the vacuum source 45 results in a subatmospheric pressure being created within the first chamber 10. The vacuum level within the chamber is typically raised to a level of at least about 30 millimeters of mercury, the precise upper level being selected by the medical practitioner attending the patient to prevent damage to either the patient's blood vessels or the interstitial tissues surrounding the blood vessels. As pointed out earlier herein, the subatmospheric pressure inside the chamber provides a pressure differential between the treated and the untreated portions of the patient's body. Once the desired vacuum level has been achived inside the first chamber 10, the constriction cuff 70 on the limb being treated may optionally be further inflated to a pressure which is sufficient to substantially block venous flow from the limb back into the patient's body, but insufficient to block arterial blood flow to the limb, i.e., less than the patient's systolic arterial blood pressure. This creates an effective driving force equal to the sum of the patient's systolic arterial blood pressure plus the absolute value of the subatmospheric pressure existing within the chamber to fill the blood vessels in the limb being treated. Because the venous flow is substantially blocked by the inflated constriction cuff 70, the pressure in the veins is caused to approach that existing within the arteries. Depending upon the initial inflation pressure of the constriction cuff, it may be necessary to gradually increase the constriction cuff inflation pressure to prevent restoration of venous blood flow as the pressure in the veins approaches that in the arteries.

In the embodiment shown in FIG. 3 both the arteries and the veins become engorged with blood to an extent even greater than with the embodiments of FIGS. 1 and 2 due to the substmospheric pressure created inside the chambers 10.

Once the limb being treated has been substantially engorged with blood and the pressure in the arteries and veins has been allowed to approach equilibrium, the restriction on venous flow imposed by the constriction cuff 70 is preferably relaxed via a signal from logic module 87 so that venous flow to the patient's body is restored. At approximately the same time, logic module 87 directs control valve 46 to vent chamber 10 to atmosphere via one of the pneumatic vent tubes.

From the foregoing description, it will be understood that the system illustrated in FIG. 3 may be operated with beneficial results with or without substantial cyclical restriction of venous blood flow by constriction cuffs 70. It is only necessary that the cuff pressure be sufficient to provide an airtight seal with the chamber 10. However, it should be recognized that increasing the cuff pressure beyond the minimum pressure required to form an airtight seal will produce a greater degree of venous constriction, up to the point of blockage of venous blood flow, which in turn will produce an opportunity for pressure equalization between the capillaries, the veins and the arteries, and hence a greater degree of blood vessel distention in the limb being treated.

Whether or not venous blood flow is blocked or substantially reduced when practicing the present invention, it is often desirable to stimulate collapse of the blood vessels at the end of each subatmospheric pressure cycle to avoid clotting.

To aid the collapse of the blood engorged veins, control valve 46 can, if so directed by logic module 87, be shifted so as to place pneumatic tube 42 in fluid communication with a secondary pneumatic pressure source shown generally at 47. Depending upon the objectives of the medical practitioner administering the treatment, the pneumatic pressure source can supply either warm air or cold air to the chamber 10 to influence vasoconstriction or dilation, as desired, e.g., cold air may prove beneficial if it is for one reason or another desired to reduce the metabolic rate in the limb being treated. Control valve 46 preferably regulates the rate of pressure build-up as well as the maximum pressure which is allowed to build up inside the chamber 10. The pressure in the chamber 10 exerts a substantially uniform compressive force on all parts of the patient's limb contained within the chamber, thereby compressing the patient's veins and expelling blood therefrom back into the patient's body. While the maximum pressure to be applied and the duration thereof should be determined by the medical practitioner attending the patient, the greater the pressure applied, the greater will be the amount of compression of the blood vessels within the limb being treated. As a result, the chance of clotting and stagnation in the limb being treated are minimized. Once the compression cycle has been completed, the chamber 10 is again vented to atmosphere and the entire engorgement cycle may be intitiated again.

In a particularly preferred embodiment of the present invention, logic module 87 performs substantially the same cycle with respect to each of the chambers on the patient's legs. However, to avoid disturbances to the balance of the patient's circulatory system, it is generally preferred that the cycles be out of phase with one another so that one of the patient's limbs is becoming engorged with blood as the other of the patient's limbs is having the blood expelled therefrom. Alternatively some extended period of time during which neither limb will be exposed to pressure or vacuum may be allowed to pass between successive treatment cycles, i.e., first treat the right leg, pause for a period of time, then treat the left leg, pause, treat right leg, etc.

It is believed that the system disclosed in FIG. 3 can be operated so as to produce several highly desirable benefits. First, the use of subatmospheric pressure on the patient's limb increases the driving force available to engorge the blood vessels in the limb being treated. This provides greater total blood flow to the limb than would be possible under the atmospheric conditions of the FIGS. 1 and 2 embodiments. Second, by utilizing the constriction cuffs 70 to restrict venous flow while the patient's limb is being engorged with blood, blood vessel distention and transmural pressure in the capillaries are greatly increased, thereby accelerating the rate of exchange of fliuds and other nutrients between the blood stream in the capillaries and the interstitial fluid surrounding the capillaries. Third, applying positive pressure to the chamber at the conclusion of the engorgement cycle (after release of the optional venous blood flow constriction on the patient's limb) allows uniform application of pressure to all parts of the patient's limb. This significantly augments venous blood flow without causing localized discomfort or irritation. Finally, by cycling the operation on a pair of limbs so that one limb is becoming engorged with blood as the other limb is expelling blood, it is believed that there will be less chance of disturbing the balance of the patient's circulatory system as the method is being practiced, since the total volume change in the blood vessels in one limb should be approximately offset by a correpsonding volume change in the opposite direction in the other limb.

Although in general, higher vacuum levels in chambers 10 will produce greater distention of the blood vessels in the limb being treated, subatmospheric pressures on the order of 100 millimeters of mercury are believed quite effective in causing the blood vessels inside the limb being treated to distend substantially and become engorged with blood. To prevent injury to either the patient's blood vessels or the interstitial tissues surrounding the blood vessels, it is preferable that some type of safety relief valve (not shown) remain in constant fluid communication with the chambers 10 to prevent excessive vacuum pressures from being developed within the chambers. In this regard, it should be noted that the teachings of the prior art (see particularly U.S. Pat. No. 4,329,985 issued to Bonchek on May 18, 1982 and hereby incorporated herein by reference) suggest that distention of human veins at pressures in excess of 500 millimeters of mercury can damage the vascular endothelium. Since little is presently known about the possible effect of extremely high vacuum pressures on the interstitial tissues surrounding the blood vessels, the medical practitioner should limit the upper level of vacuum pressure to the lowest practical value which will afford the engorgement benefits of the present invention without risking injury to the patient.

A safety relief valve (not shown) in constant fluid communication with the chambers 10 should also be provided to protect against excessive overpressure when positive pressures are employed in a treatment cycle of the present invention.

As will be appreciated by those skilled in the art, the apparatus of the present invention generally shown in FIG. 3 may be operated in a number of beneficial modes. For example, in situations where arterial blood flow in the patient is adequate, the positive pressure pulse could be utilized to augment venous blood flow without the vacuum or constriction cycles as an alternative to prior art surgical support garments or pneumatically actuated leggings. In other situations where the primary objective is to augment arterial blood flow, the positive pressure pulse could be omitted altogether. As was also pointed out, the system generally illustrated in FIG. 3 could be operated to augment blood circulation in the patient's limbs even in situations where the constriction cuffs 70 are not cyclically inflated to substantially reduce or block venous blood flow. Yet another possible mode of operation would be to operate the airtight chambers continuously at subatmospheric pressure by cyclically increasing and decreasing the vacuum level to stimulate blood vessel distention and collapse in response to the varying vacuum level inside the chamber.

Although the venous blood pressure and the arterial blood pressure will not approach equilibrium without substantial blockage of venous blood flow from the limb being treated via some form of tourniquet, all of the blood vessels in the portion of the body being subjected to subatmospheric pressure will expand somewhat relative to the blood vessels in the remainder of the patient's body which remain subject to atmospheric pressure. Accordingly, cyclically subjecting the patient's limb to subatmospheric pressure without concurrently blocking venous blood flow from the limb causes the blood vessels in the limb to exhibit a somewhat expanded cross-section during the subatmospheric portion of the cycle. Each time the chamber is vented, the somewhat enlarged blood vessels within the limb being treated seek a return to their equilibrium condition with the blood vessels in the other parts of the patient's body. This expansion and contraction of the blood vessels in the limb being treated enhances, at least to a degree, the circulation of blood to and from the limb. This approach may in fact be preferred in situations involving longer periods of treatment or in situations where it is desired to minimize any upset to the patient's cardiovascular system.

Since any collapse of the blood vessels in the limb being treated will exert a pumping action which forces the blood from the vessels in the limb being treated back into the remainder of the patient's body, the application of some type of mechanical or pneumatic pressure to the limb at the conclusion of the vacuum cycle can further enhance the circulation improvement, since it ensures a more complete collapse of the blood vessels with each complete cycle.

Whatever the mode of operating employed with the apparatus illustrated in FIG. 3, the chambers 10 are preferably removed from the patient at the conclusion of the treatment by pulling on either free tab 61 or free tab 62 of the band of encircling tape 60 which secures each end 52 of the elastomeric sleeve 50 about the perimeter of the cylindrical walls 20 of the chambers 10. As pointed out earlier herein, when the band of tape is stripped from the cylindrical wall 20 and the end 52 of the elastomeric sleeve, it encounters stress concentrating notch 55 in the edge of the elastomeric sleeve 50. Forces exerted by removal of the tape band 60 cause the stress concentrating notch 55 to initiate a self-propagating tear in a direction generally parallel to the axis of the cylindrical chamber 10. This greatly simplifies and accelerates the process of removing the chambers 10 from the patient's limbs. In addition, it permits removal of the chambers 10 while the blood pressure cuffs 70 remain inflated, should this prove to be a desirable mode of operation. The pneumatic blood pressure cuffs 70, if used at all, are thereafter released and the remainder of the elastomeric sleeve 50 is longitudinally split along the longitudinal tear initiated by stress concentrating notch 55. To reutilize the chambers 10, it is only necessary to reaffix new elastomeric sleeves to their proximal ends 31.

It is, of course, recognized that alternative means for establishing a substantially airtight seal between the vacuum chambers and the patient's body may also be employed, such as conventional adhesive tapes and the like. However, an inflatable cuff, such as pneumatic blood pressure cuff 70, is generally preferred since it aids in establising a seal at relatively low inflation pressures, yet does not result in any injury to the patient's skin upon removal. In addition, because the inflatable cuff can be used as a constricting tourniquet to cyclically block venous flow from the limb being treated, it allows practicing even the most preferred embodiments of the present method invention with a single apparatus embodiment.

To minimize any chance of misuse or injury to the patient, the method and apparatus for the present invention should be utilized only under the direction of or in accordance with a protocol established by a licensed medical practitioner who is totally familiar with both the operating parameters of the system in question and the medical history of the patient. As will be appreciated by those skilled in the art, the precise nature of the subatmospheric/atmospheric/superatmospheric pressure cycles to be employed, the number of subatmospheric/atmospheric/superatmospheric cycles, the relative duration of each, the maximum subatmospheric and superatmospheric pressures to be employed, the degree of constriction, if any, to be imposed on the limb being treated, the rate at which it is applied, and the frequency of treatment are all matters to be prescribed by the attending licensed medical practitioner to provide the desired circulation improvement without risking injury to the patient.

As will be appreciated by those skilled in the art, apparatus suitable to perform the cyclic blood vessel distention and relaxation operation in particular portions of a patient's body, as generally described herein, may vary substantially in configuration and appearance. It will be obvious to those skilled in the art that various changes and modifications can be made without departing from the spirit and scope of the invention, and it is intended to cover in the appended claims all such modifications that are within the scope of this invention.

What is claimed is:

1. A method for enhancing blood circulation in an isolated portion of a patient's body remote from the patient's heart, said method comprising the steps of:

(a) applying a constricting tourniquet to said isolated portion of the patient's body;

(b) increasing the force applied by said tourniquet to a level sufficient to reduce venous blood flow from said isolated portion of the patient's body;

(c) maintaining said force applied by said tourniquet for a period of time sufficient for the patient's arterial pressure to engorge the blood vessels contained within said isolated portion of the patient's body with blood and to substantially distend said blood vessels;

(d) loosening said tourniquet an amount sufficient to restore unrestricted venous blood flow from said isolated portion of the patient's body, thereby allowing the engorged, substantially distended blood vessels within said isolated portion of the patient's body to return from their substantially distended condition to a substantially non-distended condition and forcing blood contained within said blood vessels from said isolated portion of the patient's body;

(e) applying pressure to said isolated portion of the patient's body, thereby compressing the blood vessels within said isolated portion of the patient's body from a non-distended to an at least partially collapsed condition and further expelling blood contained within said blood vessels from said isolated portion of the patient's body; and (f) automatically repeating steps (b) through (e) in accordance with a predetermined cycle.

2. The method of claim 1, wherein said pressure is continuously applied to said isolated portion of the patient's body.

3. The method of claim 2, wherein said continuous pressure is applied by means of a surgical support garment.

4. The method of claim 1, wherein said pressure is momentarily applied to said isolated portion of the patient's body only after the loosening of said tourniquet and prior to repeating step (b).

5. The method of claim 4, wherein said pressure is applied in peristaltic fashion beginning at the distal end of said isolated portion of the patient's body and moving sequentially toward its proximal end.

6. The method of claim 5, wherein said pressure is applied by sequentially increasing the pneumatic pressure in a multiplicity of interconnected pneumatically actuated cuffs applied to said isolated portion of the patient's body.

7. The method of claim 4, wherein said pressure is applied by enclosing said isolated portion of the patient's body in an airtight chamber and subjecting the chamber to superatmospheric pressure.

8. A method for enhancing blood circulation in an isolated portion of a patient's body remote from the patient's heart, said method comprising the steps of:

(a) placing said isolated portion of the patient's body within a chamber comprised of substantially gas impervious material, said chamber being capable of supporting at least a partial vacuum;

(b) forming a substantially airtight seal between said chamber and said isolated portion of the patient's body;

(c) evacuating sufficient air from within said chamber to create a partial vacuum within said chamber;

(d) applying a constricting tourniquet to said isolated portion of the patient's body with sufficient force to substantially block venous blood flow from said isolated portion of the patient's body;

(e) maintaining said partial vacuum within said chamber while blocking venous blood flow for a period of time sufficient for the patient's arterial pressure to engorge the blood vessels contained within said isolated portion of the patient's body with blood, to substantially equalize the pressure within the arteries and veins comprising said blood vessels and to substantially distend said blood vessels;

(f) loosening said tourniquet an amount sufficient to restore venous blood flow from said isolated portion of the patient's body;

(g) allowing sufficient air to enter said chamber to substantially dissipate the partial vacuum existing within said chamber, thereby causing the engorged, substantially distended blood vessels within said isolated portion of the patient's body to return from their substantially distended condition to a substantially non-distended condition and forcing blood contained within said blood vessels from said isolated portion of the patient's body; and (h) automatically repeating steps (c) through (g) in accordance with a predetermined cycle.

9. The method of claim 8, wherein air is automatically withdrawn from and introduced into said chamber in accordance with said predetermined cycle.

10. The method of claim 9, wherein said tourniquet is pneumatically actuated and said force applied by said tourniquet is increased by increasing the pneumatic pressure in said tourniquet.

11. The method of claim 10, wherein said pneumatic pressure in said tourniquet is automatically increased and decreased in accordance with said predetermined cycle.

12. A method for enhancing blood circulation in an isolated portion of a patient's body remote from the patient's heart, said method comprising the steps of:

(a) placing said isolated portion of the patient's body within a chamber comprised of substantially gas impervious material, said chamber being capable of supporting both subatmospheric and superatmospheric pressure;

(b) forming a substantially airtight seal between said chamber and said isolated portion of the patient's body;

(c) evacuating sufficient air from within said chamber to create a partial vacuum within said chamber;

(d) applying a constricting tourniquet to said isolated portion of the patient's body with sufficient force to substantially block venous blood flow from said isolated portion of the patient's body;

(e) maintaining said partial vacuum within said chamber while blocking venous blood flow for a preiod of time sufficient for the patient's arterial pressure to engorge the blood vessels contained within said isolated portion of the patient's body with blood, to substantially equalize the pressure within the arteries and veins comprising said blood vessels and to substantially distend said blood vessels;

(f) loosening said tourniquet an amount sufficient to restore venous blood flow from said isolated portion of the patient's body;

(g) allowing sufficient air to enter said chamber to substantially dissipate the partial vacuum existing within said chamber, thereby causing the engorged, substantially distended blood vessels within said isolated portion of the patient's body to return from their substantially distended condition to a substantially non-distended condition and forcing blood contained within said blood vessels from said isolated portion of the patient's body;

(h) introducing sufficient air into said chamber to create a superatmospheric pressure within said chamber, thereby compressing the blood vessels within said isolated portion of the patient's body from a non-distended to an at least partially collapsed condition and further expelling blood contained with said blood vessels from said isolated portion of the patient's body;

(i) allowing sufficient air to exit said chamber to equalize the pressure inside said chamber with that of the surrounding atmosphere; and (j) automatically repeating steps (c) through (i) in accordance with a predetermined cycle.

13. The method of claim 12, wherein air is automatically withdrawn from and introduced into said chamber in accordance with said predetermined cycle.

14. The method of claim 13, wherein said tourniquet is pneumatically actuated and said force applied by said tourniquet is increased by increasing the pneumatic pressure in said tourniquet.

15. The method of claim 14, wherein said pneumatic pressure in said tourniquet is automatically increased and decreased in accordance with said predetermined cycle.

16. The method of claim 12, wherein said air introduced into said chamber to create a superatmospheric pressure is heated above ambient temperature prior to being introduced into said chamber.

17. The method of claim 12, wherein said air introduced into said chamber to create a superatmospheric pressure is cooled below ambient temperature prior to being introduced into said chamber.

18. Apparatus for enhancing blood circulation in an isolated portion of a patient's body remote from the patient's heart, said apparatus comprising:

(a) tourniquet means for applying a constriction to said isolated portion of the patient's body;

(b) means for increasing the force applied by said tourniquet means to a level sufficient to substantially block venous blood flow from said isolated portion of the patient's body;

(c) means for maintaining said force applied by said tourniquet while blocking venous blood flow for a period of time sufficient for the patient's arterial pressure to engorge the blood vessels contained within said isolated portion of the patient's body with blood, to substantially equalize the pressure within the arteries and veins comprising said blood vessels and to substantially distend said blood vessels;

(d) means for loosening said tourniquet means an amount sufficient to restore venous blood flow from said isolated portion of the patient's body, thereby allowing the engorged, substantially distended blood vessels within said isolated portion of the patient's body to return from their substantially distended condition to a substantially non-distended condition and forcing blood contained within said blood vessels from said isolated portion of the patient's body; and (e) means for applying pressure to said isolated portion of the patient's body to compress the blood vessels within said isolated portion of the patient's body from a non-distended to an at least partially collapsed condition and further expelling blood contained within said isolated portion of the patient's body; and (f) means for automatically actuating elements (b) through (e) in accordance with a predetermined cycle.

19. The apparatus of claim 18, wherein said means for applying pressure to said isolated portion of the patient's body applies said pressure continuously.

20. The apparatus of claim 19, wherein said means for applying pressure to said isolated portion of the patient's body comprises an elasticized surgical support garment.

21. The apparatus of claim 18, wherein said means for applying pressure to said isolated portion of the patient's body applies said pressure cyclically.

22. The apparatus of claim 21, wherein said means for applying pressure to said isolated portion of the patient's body comprises a series of interconnected, pneumatically inflatable chambers, each of said chambers encircling said isolated portion of the patient's body.

23. The apparatus of claim 18, wherein said tourniquet means comprises a pneumatically actuated pressure cuff.

24. Apparatus for enhancing blood circulation in an isolated portion of a patient's body remote from the patient's heart, said apparatus comprising:

(a) a closed chamber comprised of a substantially gas impervious material and capable of supporting at least a partial vacuum, said chamber being sized to accommodate said isolated portion of the patient's body, said chamber also including an orifice to permit insertion of said portion of the patient's body into said chamber;

(b) means for forming a substantially airtight seal between said orifice in said chamber and said portion of the patient's body;

(c) tourniquet means located near said orifice in said chamber for applying a constriction to reduce venous blood flow from said isolated portion of the patient's body;

(d) means for evacuating air from within said chamber to create a partial vacuum within said chamber;

(e) means for maintaining said partial vacuum within said chamber for a period of time sufficient for the patient's arterial pressure to engorge the blood vessels contained within the isolated portion of the patient's body with blood and to substantially distend said blood vessels;

(f) means for loosening said tourniquet means an amount sufficient to fully restore venous blood flow from said isolated portion of the patient's body;

(g) means for allowing air to enter said chamber to substantially vitiate the partial vacuum existing within said chamber, thereby causing the engorged blood vessels to return from their substantially distended condition to a substantially non-distended condition and forcing blood contained within the blood vessels from the isolated portion of the patient's body; and (h) control means for automatically actuating elements (c) through (g) in accordance with a predetermined cycle.

25. Apparatus for enhancing blood circulation in an isolated portion of a patient's body remote from the patient's heart, said apparatus comprising:

(a) a closed chamber comprised of a substantially gas impervious material and capable of supporting both subatmospheric and superatmospheric pressure, said chamber being sized to accommodate said isolated portion of the patient's body, said chamber also including an orifice to permit insertion of said portion of the patient's body into said chamber;

(b) means for forming a substantially airtight seal between said orifice in said chamber and said portion of the patient's body;

(c) tourniquet means located near said orifice in said chamber for applying a constriction to reduce venous blood flow from said isolated portion of the patient's body;

(d) means for evacuating air from within said chamber to create a partial vacuum within said chamber;

(e) means for maintaining said partial vacuum within said chamber while restricting venous blood flow for a period of time sufficient for the patient's arterial pressure to engorge the blood vessels contained within the isolated portion of the patient's body with blood and to substantially distend said blood vessels;

(f) means for loosening said tourniquet means an amount sufficient to fully restore venous blood flow from said isolated portion of the patient's body;

(g) means for allowing air to enter said chamber to substantially vitiate the partial vacuum existing within said chamber, thereby causing the engorged blood vessels to return from their substantially distended condition to a substantially non-distended condition and forcing blood contained within the blood vessels from the isolated portion of the patient's body;

(h) means for introducing sufficient air into said chamber to create a superatmospheric pressure within said chamber, thereby compressing the blood vessels within said isolated portion of the patient's body from a non-distended to an at least partially collapsed condition and further expelling blood contained within said blood vessels from said isolated portion of the patient's body;

(i) means for allowing sufficient air to exit said chamber to equalize the pressure inside said chamber with that of the surrounding atmophere; and (j) control means for automatically actuating elements (c) through (i) in accordance with a predetermined cycle.

26. The apparatus of claim 25, including means for heating said air used to create said superatmospheric pressure above ambient temperature prior to introducing it into said chamber.

27. The apparatus of claim 25, including means for cooling said air used to create said superatmospheric pressure below ambient temperature prior to introducing it into said chamber.

28. The apparatus of claim 25, including safety means in fluid communication with said chamber to limit the subatmospheric pressure which can be established within said chamber to a level which is incapable of injuring the patient.

29. The apparatus of claim 25, including safety means in fluid communication with said chamber to limit the superatmospheric pressure which can be established within said chamber to a level which is incapable of injuring the patient.

* * * * *

UNITED STATES PATENT AND TRADEMARK OFFICE

CERTIFICATE OF CORRECTION

PATENT NO. : 4,738,249

DATED : April 19, 1988

INVENTOR(S) : E. KELLY LINMAN and EUGENE WEINSHENKER

It is certified that error appears in the above-identified patent and that said Letters Patent is hereby corrected as shown below:

Column 3, line 59, "is" should read -- it --.

Column 4, line 24, "substmospheric" should read -- subatmospheric --.

Column 4, line 55, "eqalization" should read -- equalization --.

Column 4, lines 58-59, "detended" should read -- distended --.

Column 6, line 14, "reease" should read -- release --.

Column 7, line 23, "teh" should read -- the --.

Column 7, line 27, after "cycle" delete the comma(,) and insert therefor -- a period(.) --.

Column 10, line 12, "at" should read -- as --.

Column 10, line 28, "one" should read -- on --.

Column 11, line 11, "achived" should read -- achieved --.

Column 11, line 33, "substmospheric" should read -- subatmospheric --.

Column 12, lines 66-67, "correpsonding" should read -- corresponding --.

Column 14, line 18, "operating" should read -- operation --.

Claim 12, column 17, line 8, "preiod" should read -- period --.

Signed and Sealed this

Fourth Day of October, 1988

*Attest:*

DONALD J. QUIGG

*Attesting Officer*

*Commissioner of Patents and Trademarks*